United States Patent [19]
Webster

[11] Patent Number: 5,274,405
[45] Date of Patent: Dec. 28, 1993

[54] WIDE ANGLE VIEWING SYSTEM

[75] Inventor: John A. Webster, Mt. Vernon, Wash.

[73] Assignee: Concept Vision Systems, Inc., Mount Vernon, Wash.

[21] Appl. No.: 755,025

[22] Filed: Sep. 4, 1991

Related U.S. Application Data

[63] Continuation-in-part of Ser. No. 417,641, Oct. 14, 1989, Pat. No. 5,123,726, Continuation-in-part of Ser. No. 121,441, Nov. 17, 1987, Pat. No. 4,874,235.

[51] Int. Cl.⁵ .............................................. G02C 1/00
[52] U.S. Cl. .................................... 351/158; 351/201
[58] Field of Search ................ 351/158, 201; 359/449, 359/464, 631; 358/88, 92

[56] References Cited

U.S. PATENT DOCUMENTS

| | | | |
|---|---|---|---|
| 3,166,395 | 1/1965 | Hicks, Jr. | 65/4 |
| 3,222,204 | 12/1965 | Weber et al. | 117/27 |
| 3,356,002 | 12/1967 | Raitiere | 95/18 |
| 3,439,972 | 4/1969 | Ratliff, Jr. | 350/131 |
| 3,514,871 | 6/1970 | Tucker | 35/12 |
| 4,048,653 | 9/1977 | Spooner | 358/104 |
| 4,257,062 | 3/1981 | Meredith | 358/81 |
| 4,348,185 | 9/1982 | Breglia et al. | 434/43 |
| 4,406,532 | 9/1983 | Howlett | 354/114 |
| 4,632,508 | 12/1986 | Connelly | 350/174 |
| 4,709,263 | 11/1987 | Brumage | 358/88 |
| 4,714,320 | 12/1987 | Banbury | 350/174 |
| 4,723,160 | 2/1988 | Connelly | 358/103 |
| 4,740,836 | 4/1988 | Craig | 358/92 |
| 4,743,200 | 5/1988 | Welch et al. | 434/43 |
| 4,846,154 | 7/1989 | MacAnally et al. | 128/6 |

FOREIGN PATENT DOCUMENTS 1103961  4/1961  Fed. Rep. of Germany .

OTHER PUBLICATIONS

Meigs, James B, 3-D TV Comes Home, *Popular Mechanics*, Aug., 1987.

Primary Examiner—Bruce Y. Arnold
Assistant Examiner—Hung Xuan Dang
Attorney, Agent, or Firm—Christensen, O'Connor, Johnson & Kindness

[57] ABSTRACT

Disclosed is a viewing system (30) for displaying and viewing stereoscopic images to a viewer's full field of view. The viewing system includes an image display assembly (32) including display surfaces (34) for displaying images primarily to the viewer's area of visual attention and display surfaces (36) for displaying images primarily to the viewer's area of peripheral vision. The display surfaces are mounted in relatively close proximity to the viewer's eyes. The viewing system further includes an optical component (33) having optical systems (40 and 42) for focusing images displayed on the display surfaces (34 and 36), respectively, to the viewer's eyes.

21 Claims, 10 Drawing Sheets

WIDE ANGLE VIEWING SYSTEM

GOVERNMENT RIGHTS

This invention was made with government support under Contract DAAH01-89-C0242 C-0817 awarded by the Defense Advanced Research Projects Agency. The government has certain rights in this invention.

This application is a continuation-in-part of application Ser. No. 07/417,641, filed Oct. 14, 1989, now U.S. Pat. No. 5,123,726 which is a continuation-in-part of application Ser. No. 07/121,441, filed Nov. 17, 1987, now U.S. Pat. No. 4,874,235, the benefit of the filing of which is hereby claimed under 35 U.S.C. §120. U.S. application Ser. No. 07/417,641 and U.S. Pat. No. 4,874,235 are hereby incorporated by reference.

FIELD OF THE INVENTION

The present invention relates to an optical viewing apparatus for viewing images and, more particularly, to an apparatus which extends the perceptible viewing field presented to a viewer.

BACKGROUND OF THE INVENTION

The quality of an optical system depends largely upon the field of view, the correctness of the colors, and the clarity and intensity of the images presented to a viewer. Optical technicians are continually striving to improve these factors to provide the most realistic image possible within physical and economical constraints. The present invention is directed toward extending the field of view presented to a viewer into the peripheral viewing areas while maintaining current standards for image clarity, color, and intensity. The invention is further directed toward an apparatus that provides three-dimensional viewing, i.e., stereoscopic viewing, to a viewer.

Three-dimensional viewing systems are rapidly developing, due to the vast areas in which such technology is useful. Three-dimensional viewing systems duplicate normal visual perception and have applications in the areas of: undersea (submersible) maintenance and search equipment; robotics; high-security surveillance; hazardous materials handling; entertainment; training simulator technologies; and education, to name a few. The goal of such systems is to substitute a computer-generated, recorded, or real-time remote reality for the user's current reality. Such systems may include audio, visual, and motion inputs to the user in order to create a more realistic experience. The video aspect of such systems is known as stereoscopic viewing. Stereoscopy provides two views, i.e., a left and a right view, that are integrated by the viewer to give the impression of viewing three-dimensional objects.

A stereoscopic viewing system that presents images to a viewer's full field of view is desirable because these images will be more realistic, and thus will more closely resemble the actual environment being viewed. The field of view of a human eye is defined with respect to the head being stationary and the eye free to rotate about its socket. Generally, the eye perceives a relatively small object area with maximum visual acuity. More specifically, the macula latea, and within the macula latea, the fovea centralis region of the retina provides the sharpest and most detailed information of an object. Thus, the eyeball is continuously moving so that light coming from an object of primary interest falls upon the fovea centralis region of the retina. In terms of the field of view of an eye, the cone-shaped area to which an eye can scan and perceive with maximum visual acuity, i.e., light from this area falls on the macula/fovea region of the retina during the eye scan, is defined as the area of visual attention of the eye. The area falling outside the area of visual attention, but still perceptible by the eye as it scans the area of visual attention, is defined as the area of peripheral vision. The field of view of the eye is thus the area of visual attention coupled with the area of peripheral vision, with the head stationary and the eye utilizing normal eye scan.

The actual size of the area comprising a full field of view for a person depends, in part, upon the facial and other physical characteristics of the individual. For an average adult the area of visual attention for one eye is on the order of 120° horizontal by 120° vertical. It will be appreciated that the area of visual attention may be more appropriately regarded as cone-shaped with the 120° by 120° description being an approximation thereof. The left and right eyes perceive approximately the same objects in this 120° by 120° field of view, albeit from a slightly different perspective. The left and right areas of peripheral vision provide on the order of 60° horizontal by 120° vertical perception on the left and right sides of the area of visual attention, respectively, as the eyes scan the areas of visual attention. It is noted that the nose blocks the right eye from perceiving objects that fall into the left area of peripheral vision, and the left eye from perceiving objects that fall into the right area of peripheral vision.

The horizontal portions of the full field of view for an average adult right eye 16 are illustrated in FIG. 1. The angle $\beta$ depicts the area that is perceived with visual acuity as the eye scans the area of visual attention. The eye 16 is shown positioned at the leftmost and rightmost boundaries of its scan. Light reflected by objects within the cone-shaped region bounded by the angle $\theta$ would fall upon the macula/fovea region of the retina during the scan. The area of peripheral vision for the eye is depicted by the angle $\beta$, in the far right portion of FIG. 1, encompassing the area that the eye can perceive, but that does not fall within the area of visual attention. As is stated above, for the average adult eye the angles $\theta$ and $\beta$ are on the order of 120° and 60°, respectively. An illustration of the field of view for the left eye would be similar to FIG. 1, with the nose 17 and peripheral area (angle $\beta$) transposed. The full field of view for an average adult can thus be approximated as 120° vertical by 240° horizontal, the horizontal portion being equal to the area encompassing a 120° field of visual attention (essentially the same objects perceived by each eye) and two 60° fields of peripheral vision (each perceived by one eye only).

Optical systems have historically disregarded the peripheral fields of vision. Attempts to present a portion of the areas of peripheral vision have generally been expensive, room-size systems. Other efforts have focused on compressing a wide image into a small field of view. This compression of images by useful to the viewer in that the viewer can perceive a greater amount of information than with those systems that have a one-to-one correspondence between objects and images. However, the image generally suffers from distortion and other distracting characteristics. For example, FIG. 2 depicts an optical system 18 positioned in front of an eye 19. The optical system 18 compresses what is in reality 130° of horizontal view (Image Plane) onto a viewing system that presents a field of view on the order of 100° (angle α) to the viewer. This type of viewing system generally does not display images to the peripheral area (generally designated at 20), but this area is still perceived by the eye. The lack of visual information in the peripheral field of view is both distracting and annoying to a viewer, and takes away from the concept of a total visual reality environment.

SUMMARY OF THE INVENTION

The present invention is an apparatus for viewing images by an eye of a viewer, the viewer's eye having a field of view that is defined with respect to the head being stationary and the eye free to rotate in its socket. The field of view of an eye includes (1) the area of visual attention, where objects may be perceived with detail and sharpness, and (2) the area of peripheral vision, i.e., that area that falls outside the area of visual attention but which is still perceptible by the eye as it scans the area of visual attention. The present invention provides an apparatus that displays images to both the area of visual attention and the area of peripheral vision of the eye.

The apparatus comprises an image display component that receives signals representative of first and second images to be viewed and displays the images on first and second display surfaces. The apparatus further comprises an optical component for focusing the images displayed on the first and second display surfaces to the eye of the viewer. The optical component includes first and second optical systems, with each optical system having an exit pupil located near the viewer's eye. The first optical system receives light from the first display surface and conveys the light to the exit pupil of the first optical system such that the eye can see the first image on the first display surface. Similarly, the second optical system receives light from the second display surface and conveys the light to the exit pupil of the second optical system such that the eye can see the second image on the second display surface.

In accordance with one aspect of the invention, the first optical system focuses images from the first display surface primarily to the area of visual attention of the eye and the second optical system focuses images primarily to the area of peripheral vision of the eye. First and second image gatherers on cameras are used to gather images for display on the first and second display components, respectively. The apparatus further includes an enclosure for the image display and optical components that aligns the components with the viewer's eye.

In accordance with another aspect of the invention, the apparatus is a stereoscopic viewing system having at least four display surfaces and four optical components for displaying images presented on the display surfaces to the viewer's eyes. Each optical component has an exit pupil. The components for a single eye include at least two display surface/optical component pairings; the display surfaces display the full or nearly the full field of view to the eye. The display and optical components for the eyes are housed in a lean-into device that positions the eyes in such a way that the eyes can perceive the images displayed on the display surfaces through the exit pupils of the optical components.

In another (non-stereoscopic) embodiment of the invention, the apparatus comprises a concave display surface that has a first surface area for displaying images within the area of visual attention and a second surface area for displaying images within the area of peripheral vision. An optical component is positioned between the display surface and a viewer's eye to focus images presented thereon to the viewer's eye. The optical component includes a plurality of exit pupils such that the eye can perceive displayed images positioned within the exit pupils.

In another embodiment of the invention, the apparatus is a stereoscopic viewing system for displaying and viewing stereoscopic images. The images to be displayed are gathered and processed as left and right images that are differentiated by the image display component and displayed on left and right curved screens. The screens are positioned in close proximity to the viewer's eyes and alignment aids are included to maintain the screens in proper orientation with respect to the viewer's head. An optical component focuses the images displayed on the screens to the left and right eyes of the viewer. The optical component has a plurality of exit pupils located near the eyes such that when the eyes are properly positioned within the exit pupils, the displayed images are clearly perceived by the eyes.

BRIEF DESCRIPTION OF THE DRAWINGS

The various features and advantages of the invention will be understood in view of the following description taken in conjunction with the accompanying drawings in which.

DETAILED DESCRIPTION OF THE PREFERRED EMBODIMENT

The preferred embodiments of the present invention are stereoscopic (binocular) viewing systems which display images to both the area of visual attention and the area of peripheral vision of each eye. However, it is noted that the viewing system may also be monocular or biocular, depending upon the needs of the intended user. Thus, while this discussion is generally directed toward stereoscopic viewing, it is realized that non-stereoscopic viewing may be practiced in accordance with this disclosure.

Figure 2:
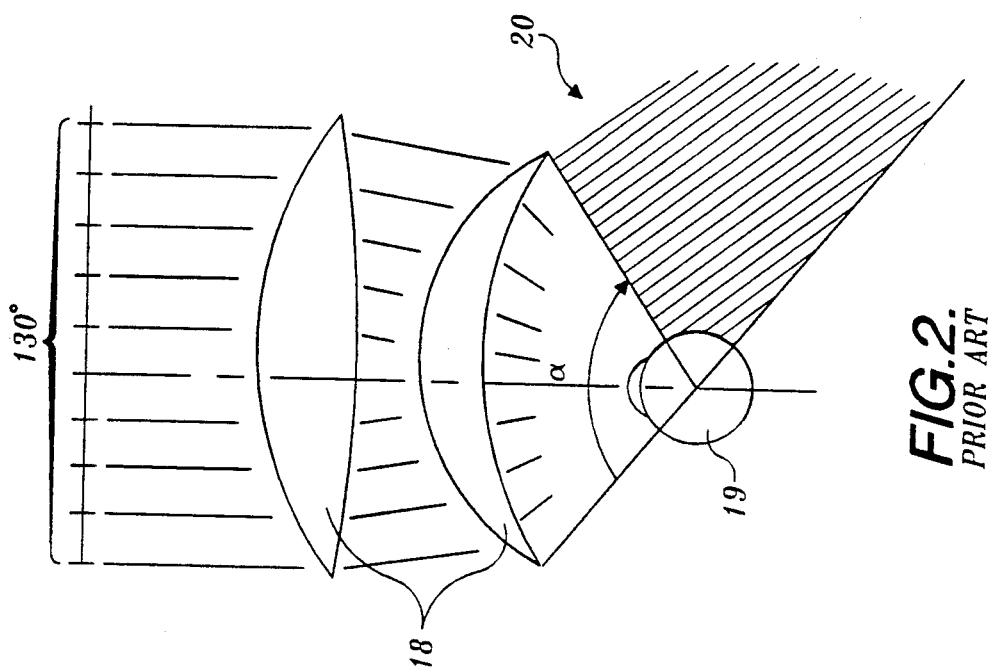
FIG. 2 is an illustration of a prior art optical system that displays images to a viewer's area of visual attention but not to the viewer's area of peripheral vision.
Figure 1:
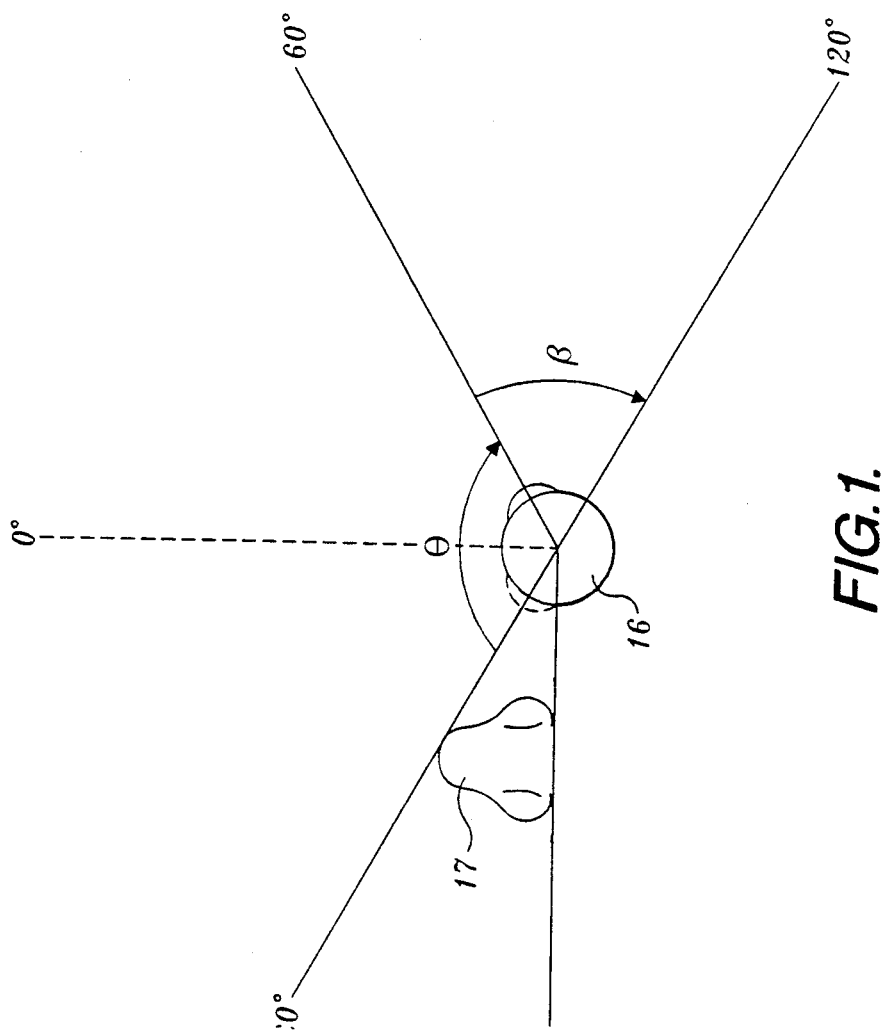
FIG. 1 is an illustration of the field of view of an average adult right eye with the head stationary and the eye utilizing normal eye scan, the field of view including an area of visual attention subtended by angle $\theta$ and an area of peripheral vision subtended by angle $\beta$.
Figure 3:
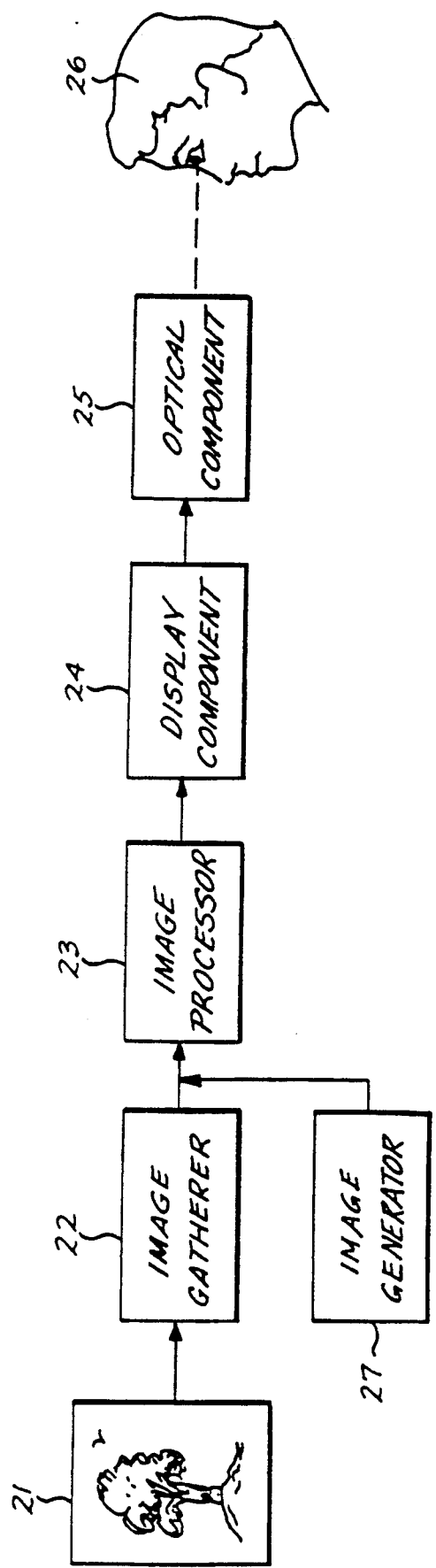
FIG. 3 is a block diagram of a monocular viewing system of which the present invention is a component.

The components of a monocular viewing system in accordance with the invention are illustrated in a generalized fashion in FIG. 3. An image 21 is gathered by an image gatherer or camera 22. The image includes objects that would fall within both the viewer's area of visual attention and area of peripheral vision for the eye if seen by a viewer in a normal fashion. The image is processed by an image processor 23 into multiple images (i.e., at least two) for displaying the image to both the viewer's area of visual attention and area of peripheral vision. The images, once gathered, are displayed on display component(s) 24 in a manner that continues to differentiate the processed images to provide viewing to each visual area. An optical component 25 is positioned between the display component 24 and a viewer 26 to properly focus the displayed images to the eye of the viewer.

A suitable image processor 23 is, for example, a computer which digitizes the information from the image gatherer 22 into image information that is presented to a viewer's (1) area of visual attention and (2) area of peripheral vision. Image processors for use in digitizing visual information for subsequent display on one or more display surface are known in the art. As an alternative to using the image gatherer 22, in certain applications, e.g., training simulator technologies, it is desirable to use an image generator 27 to provide images to the image processor 23. A suitable image generator is, for example, a computer that utilizes a prestored graphics database to generate real-time images in accordance with the desired application of the viewing system.

Figure 4:
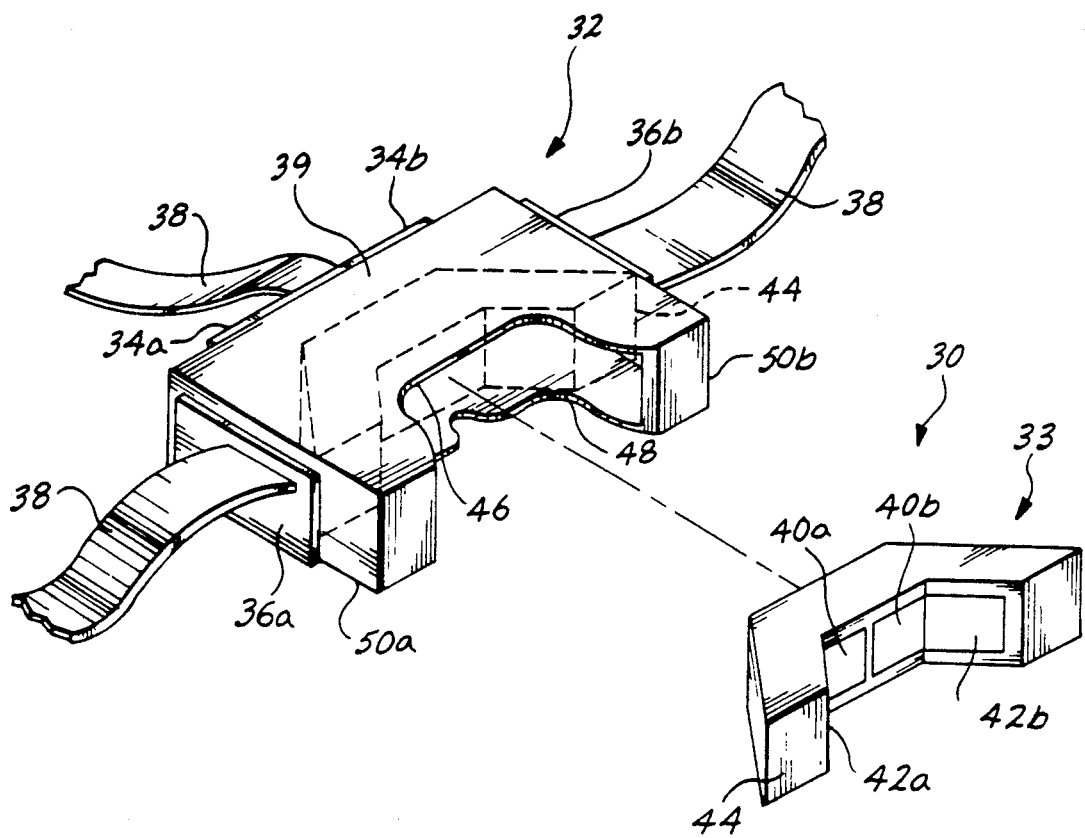
FIG. 4 is an exploded pictorial view of first preferred embodiment of a stereoscopic viewing system in accordance with the invention.

FIG. 4 illustrates a first preferred embodiment of a stereoscopic viewing system 30 in accordance with the invention. The stereoscopic viewing system 30 of FIG. 4 incorporates the display component 24 and optical component 25 of FIG. 3 for both eyes of a viewer. The same reference numerals will be used throughout the present description to identify equivalent left and right components. It is to be understood that subreferences (a) and (b) refer to left and right components, respectively.

The stereoscopic viewing system 30 comprises an image display assembly 32 and an optical component 33 for focusing the images displayed on the display assembly to the eyes of a viewer. The display assembly 32 includes display surfaces or screens 34a and 34b which display images for presentation to a viewer's area of visual attention for the left and right eyes, respectively. Display component 32 also includes display surfaces or screens 36a and 36b which display images for presentation primarily to the viewer's left and right areas of peripheral vision, respectively. The display surfaces 34 and 36 receive image information from an image processor through electrical cables 38. The center cable 38 provides image information to each display surface 34a and 34b using different conductive signal paths.

The display surfaces 34 and 36 are positioned within an opaque enclosure 39 such that they do not optically interfere with one another. The display surfaces are mounted within the enclosure 39 through methods known in the art and appropriate for the particular devices used. The enclosure 39 aids in removing external indications of actual reality from the viewer's perception, e.g., ambient light, and in maintaining the relative orientation of the display surfaces 34 and 36 with respect to the viewer's head. To provide stereoscopic viewing, the display surfaces must be properly positioned with respect to the viewer's eyes. By placing the display assembly 32 and optical component 33 relatively close to the viewer's eyes, the left eye views images exclusively from the display surfaces 34a and 36a and the right eye views images exclusively from the display surfaces 34b and 36b, thus allowing the presentation of stereoscopic images. Suitable devices for use as the display surfaces 34 and 36 include flat panel displays, such as light-emitting diodes (LEDs) or liquid crystal displays (LCDs); cathode ray tubes (CRTs); or subtractive and additive light valve projection systems.

The display surfaces 34 and 36 are dimensioned to present images to a substantial portion of the full field of view of a viewer. The physical dimensions of the display surfaces are not of great importance as long as the surfaces do not physically interfere with one another and an appropriate optical component can be tailored to properly focus the images presented to the viewer's eyes. In an actual embodiment, the display surfaces 34 and 36 are each on the order of 2" square. It is noted that the display surfaces 34a and 34b may, alternatively, be a single display surface with the images appearing thereon separated into left and right images through a suitable means known in the art, e.g., using two projection devices or digitizing the image information into left and right coordinates displayed on a CRT.

Due to the relatively close proximity of the display assembly 32 to the viewer's eyes, a viewer with relatively normal vision will have difficulty focusing on the images presented. The optical component 33 provides the needed optical correction such that the eyes can focus on the displayed images. The optical component 33 includes front-view optical systems 40a and 40b and side-view optical systems 42a and 42b for focusing images displayed to the display surfaces 34a, 34b, 36a and 36b, respectively. The optical systems 40 and 42 are contained within a housing unit 44 that fits into the enclosure 39 of the stereoscopic viewing system 30. Alternatively, the optical systems 40 and 42 may be mounted directly into the enclosure 39.

The display assembly 32 is a lean-into device having a forehead brace 46, a lower brace 48, and left and right temporal extensions 50a and 50b, respectively. Preferably, the braces 46 and 48 are formed of a semipliable or padded material. The forward brace 46 is shaped to conform to a viewer's forehead. The lower brace 48 is shaped to conform to the viewer's nose and cheek bones. The temporal extensions 50 extend from the display surfaces 36 toward the viewer's ears and provide structural support for these surfaces.

To view images with the stereoscopic viewing system, a viewer positions his or her face against the braces and between the extensions, thus positioning the eyes in close proximity to the display surfaces 34 and 36 and optical component 33. The padding on the braces conforms to the viewer's face providing a proper relationship for the face and allowing the viewer to remain in a comfortable position. As will be appreciated, the viewing system 30 can also be encased in a face mask or mounted within a helmet as an alternative to the disclosed lean-into device.

Figure 5:
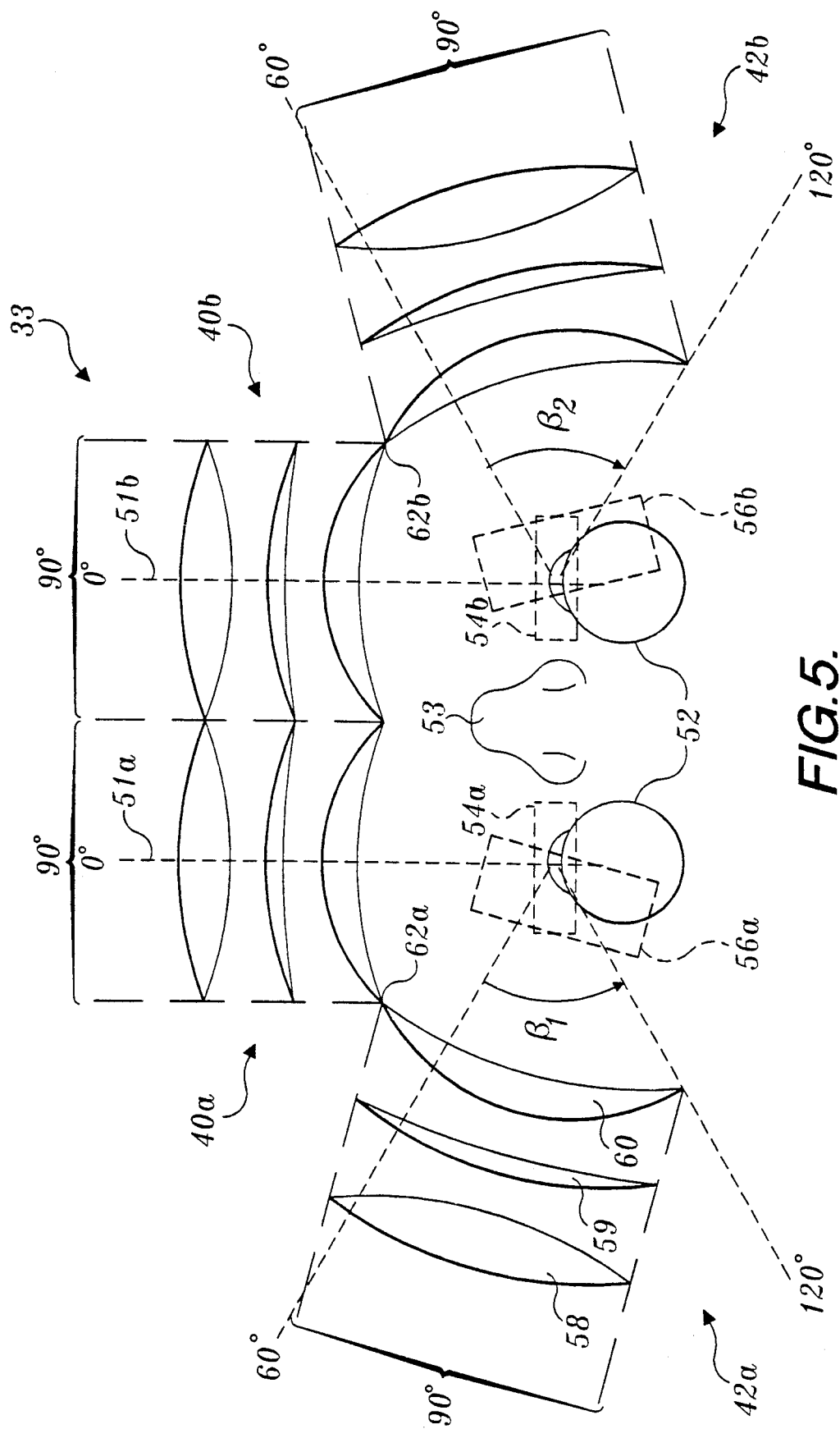
FIG. 5 is a schematic view depicting the optical components as illustrated in FIG. 4.

FIG. 5 illustrates one embodiment of the optical component 33, including the optical systems 40 and 42. The optical systems 40a and 40b are aligned with the centerlines of vision 51a and 51b of the eyes 52 of a viewer, when the viewer's face is positioned into the stereoscopic viewing system. The centerlines of vision 51 are defined with respect to the eyes looking straight (forward) toward the optical systems 40. The optical systems 42 are positioned in relation to the optical systems 40 such that the eyes can perceive images through the optical systems 42. The viewer's nose 53 prevents the left eye from viewing images displayed to the right eye, and vice versa.

The optical systems 40 and 42 comprise a number of converging lenses that allow the eyes of the viewer to clearly see images displayed on the display surfaces. Each optical system 40 and 42 forms a cylindrical exit pupil that is located near the viewer's eyes. Optical systems 40a and 40b form exit pupils 54a and 54b, respectively. Optical systems 42a and 42b form exit pupils 56a and 56b, respectively. Generally, the exit pupil of an optical system defines a region in space. An eye positioned within the exit pupil of an optical system will perceive images presented on a display surface as they are focused through the optical system. As the eye is moved near the boundaries of the exit pupil, displayed images become distorted and eventually become imperceptible as the eye is positioned further from the center of the exit pupil.

The optical component 33 and display assembly interact such that the viewer's eyes 52 are positioned within the region bounded by the exit pupils 54 and 56 when the viewer's face is placed into the display assembly. The region bounded by the exit pupils 54 and 56 is of sufficient size to provide clear perception of the displayed images, taking into account normal eye movement or scan, the facial characteristics of the intended users of the viewing system and, if practicable, allowing at least some freedom of movement of the viewer's head relative to the viewing system.

Standard optical lenses are used in the optical systems 40 and 42, with the amount of convergence, i.e., optical correction, dependent upon the spatial relationship of (1) the viewer's eyes, (2) the optical systems, and (3) the display surfaces. In the embodiment of FIG. 5, each optical system comprises three lenses. For example, optical system 42a includes a biconvex lens 58, a meniscus convex lens 59 and a meniscus convex lens 60, the meniscus convex lens 60 being closest to the eye. The number and optical characteristics of the lenses shown are illustrative only; other lens configurations may be implemented as long as they exhibit the correct optical convergence and a sufficient exit pupil is provided by the lens or lenses.

The stereoscopic system displays images to the full field of view of the viewer, i.e., 120° vertical by 240° horizontal. Each optical system 40 and 42 focuses a 120° vertical by 90° horizontal field of view to the eyes of the viewer. The display surfaces of FIG. 4 correspondingly display the full field of view in 120° vertical by 90° horizontal portions. For example, to the viewer's left in FIG. 4, display surface 36a displays the full left area of peripheral vision and 30° (horizontal) of the left area of visual attention, and display surface 34a displays the remaining 90° (horizontal) of left area of visual attention.

The horizontal portions of the full field of view, corresponding to images to be displayed by the display surfaces, are depicted generally at FIG. 5. Each optical system 40a, 40b, 42a and 42b focuses a 90° horizontal by 120° vertical field of view. Optical systems 42a and 42b focus a 60° horizontal field to the peripheral areas ($\beta_1$ and $\beta_2$) and a 30° horizontal field to the areas of visual attention (adjacent the areas subtended by $\beta_1$ and $\beta_2$) for the left and right eyes, respectively. The optical systems 40a and 40b focus a 90° horizontal field to the left and right areas of visual attention, respectively. Thus, images are presented and focused to the 60° left peripheral area, the 120° area of visual attention for each eye, and the 60° right peripheral area. Hence, the optical component 33 focuses images to the full field of view of a viewer, with the left eye perceiving approximately the same image information as the right eye within the areas of visual attention.

It is noted that a discontinuity will exist in the images at 62a and 62b, where the optical systems 40 are connected to the optical systems 42. The discontinuities do not pose a significant distraction because the mind tends to discount the distortion caused thereby and concentrate on the images presented by the display assembly. It is realized, however, that in the embodiment of FIG. 5 the discontinuities are each within the viewer's area of visual attention. The physical connection of the lenses can be moved outwardly, to the areas of peripheral vision, by using a single optical system/display surface pairing for the total area of visual attention, i.e., 120° vertical by 120° horizontal, for each eye. For example, in an alternative embodiment the stereoscopic viewing system is implemented using optical system/display surface pairings configured, horizontally, on a (1) 60° left peripheral, (2) 120° left area of visual attention, (3) 120° right area of visual attention, and (4) 60° right peripheral vision basis. The vertical portion is still 120° for each pairing. The trade-off to such a system is the increased cost and complexity associated with providing an optical system that has an increased field of view, i.e., the optical systems in the alternative embodiment described directly above must provide a 120° field of view as opposed to a 90° field of view in the embodiment of FIG. 5. However, such a configuration may clearly be advantageous in certain applications.

Figure 6:
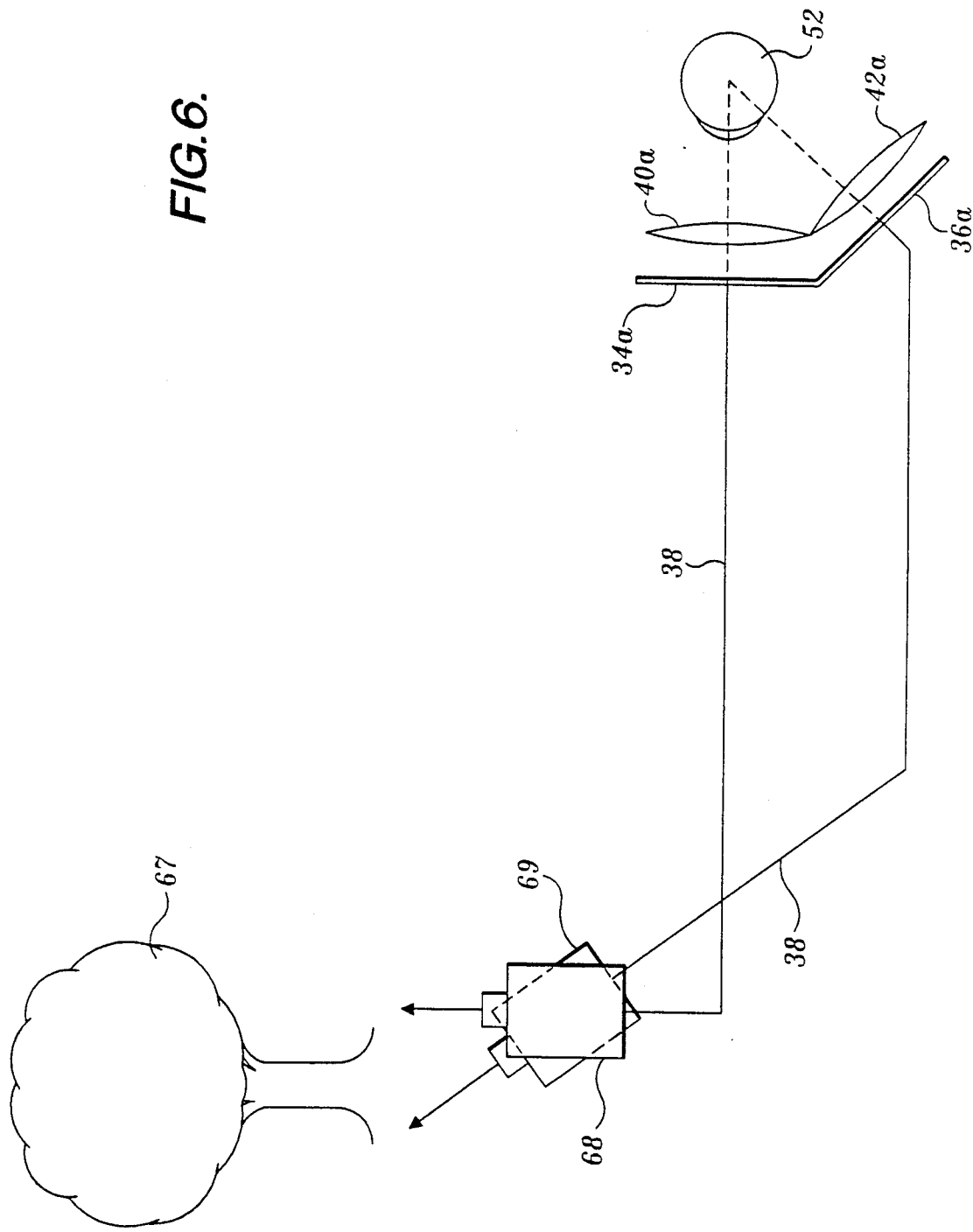
FIG. 6 is a schematic view of a monocular viewing system utilizing multiple image gatherers, in accordance with the invention.

With reference to FIG. 6, in an alternative embodiment to the single image gatherer of FIG. 3, multiple separate image gatherers are used to gather image information 67 from the areas of visual attention and peripheral vision for display to a viewer's eye. In FIG. 6, the left eye 52 of a viewer is depicted. Multiple image gatherers may comprise, for example, front and side view cameras 68 and 69 that are mounted in a predetermined spatial relationship such that the front view camera 68 gathers information falling in the area of visual attention and the side view camera 69 gathers information falling primarily in the area of peripheral vision. The images from the front and side view cameras 66 and 67 are displayed on the display surfaces 34a and 36a, respectively. The displayed images (from display surfaces 34a and 36a) are focused by the optical elements 40a and 42a, respectively, to the eye 52.

The stereoscopic viewing system provides full field of view imaging by utilizing an optical component having at least two exit pupils for each eye. In contrast, the use of a single exit pupil system generally causes problems of distortion and difficulty in presenting images to the full field of view. As is known in the art, as the field of view of an optical system is increased, the images focused therethrough become increasingly susceptible to distortion. Indeed, there are limits to the field of view that can be shown through an optical system having a single exit pupil. Further, the cost and complexity of an optical system are generally also increased as the field of view of the optical system is enlarged. In contrast, the invention provides an optical system having multiple, i.e., at least two, exit pupils for each eye to establish full field of view imaging and to minimize distortion, cost and complexity of the optical systems used to focus the images.

Figure 7:
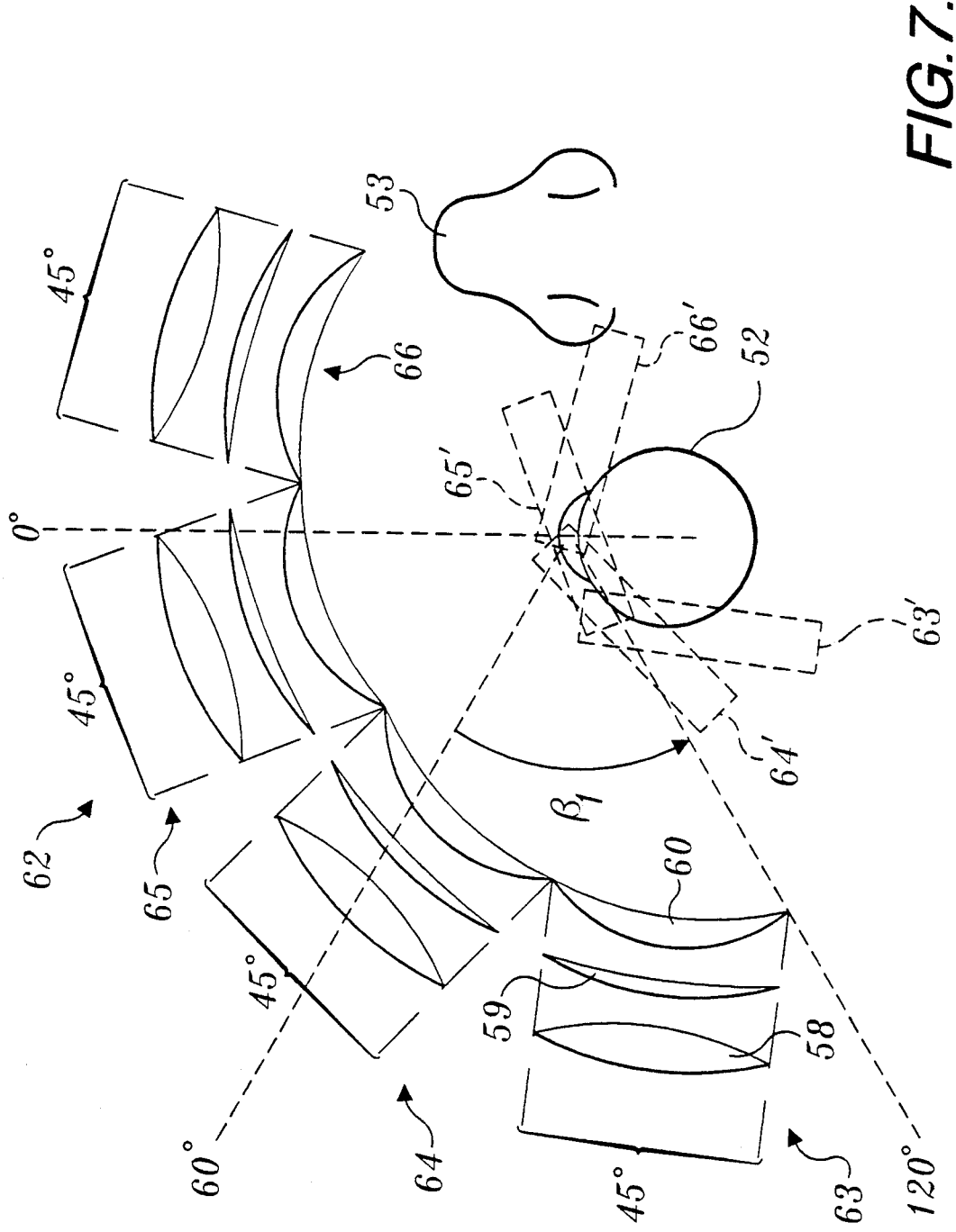
FIG. 7 is a schematic view depicting an optical component for a left eye for use with a second preferred embodiment of a viewing system in accordance with the invention.

It is noted that a different configuration for the optical system/display surface pairings than those disclosed may be implemented. Moreover, stereoscopic viewing systems utilizing more than two optical systems for each eye, each having its own exit pupil, may also be implemented. As an illustrative example, instead of using two optical system/display surface pairings for each eye (as in FIG. 4), FIG. 7 depicts an optical component 62 having four optical system/display surface pairings for each eye. Only the left eye 52 and associated optical elements are depicted in FIG. 7.

The optical component 62 includes four optical elements 63, 64, 65, and 66, each having an exit pupil 63', 64', 65', and 66', respectively. Each optical element focuses a 45° field of view from their respective display surfaces (not shown). The display surfaces also display 45° field of view image information. The optical elements are similar to those of FIG. 5, although of smaller dimensions. For example, optical system 63 includes a biconvex lens (58), a meniscus convex lens (60), and meniscus convex lens (62).

With regard to the horizontal portion of the field of view, optical element 63 focuses images falling in the left area of peripheral vision. Optical element 64 focuses images falling in the remaining portion of the left area of peripheral vision (i.e., approximately 15°) and approximately 45° of the area of vision attention. Optical elements 65 and 66 focus the remaining area of visual attention (i.e., 90°). Thus, the optical component 62 focuses the full field of vision for the left eye 52 of a viewer.

Increasing the number of optical elements/display surface pairings is advantageous in certain applications. For example, high resolution cathode ray tubes (CRTs) are readily available in ½" round dimensions. A stereoscopic system may be implemented in accordance with the invention to use a plurality of ½" round CRTs for each eye, providing high resolution imagery to the eye. Each display surface (CRT) would include an optical system to focus its displayed images. Such a system could have problems with distortion where the optical systems are connected together.

The desirableness of further increasing the number of display surfaces is fully appreciated by incorporating all of the display surfaces into a single curved surface that wraps around a viewer's eye. As before, the images depicted on each display surface must be focused to allow a viewer to perceive displayed images. The implementation of a curved surface with an optical component having multiple exit pupils to focus images thereon is depicted in FIG. 8.

Figure 8:
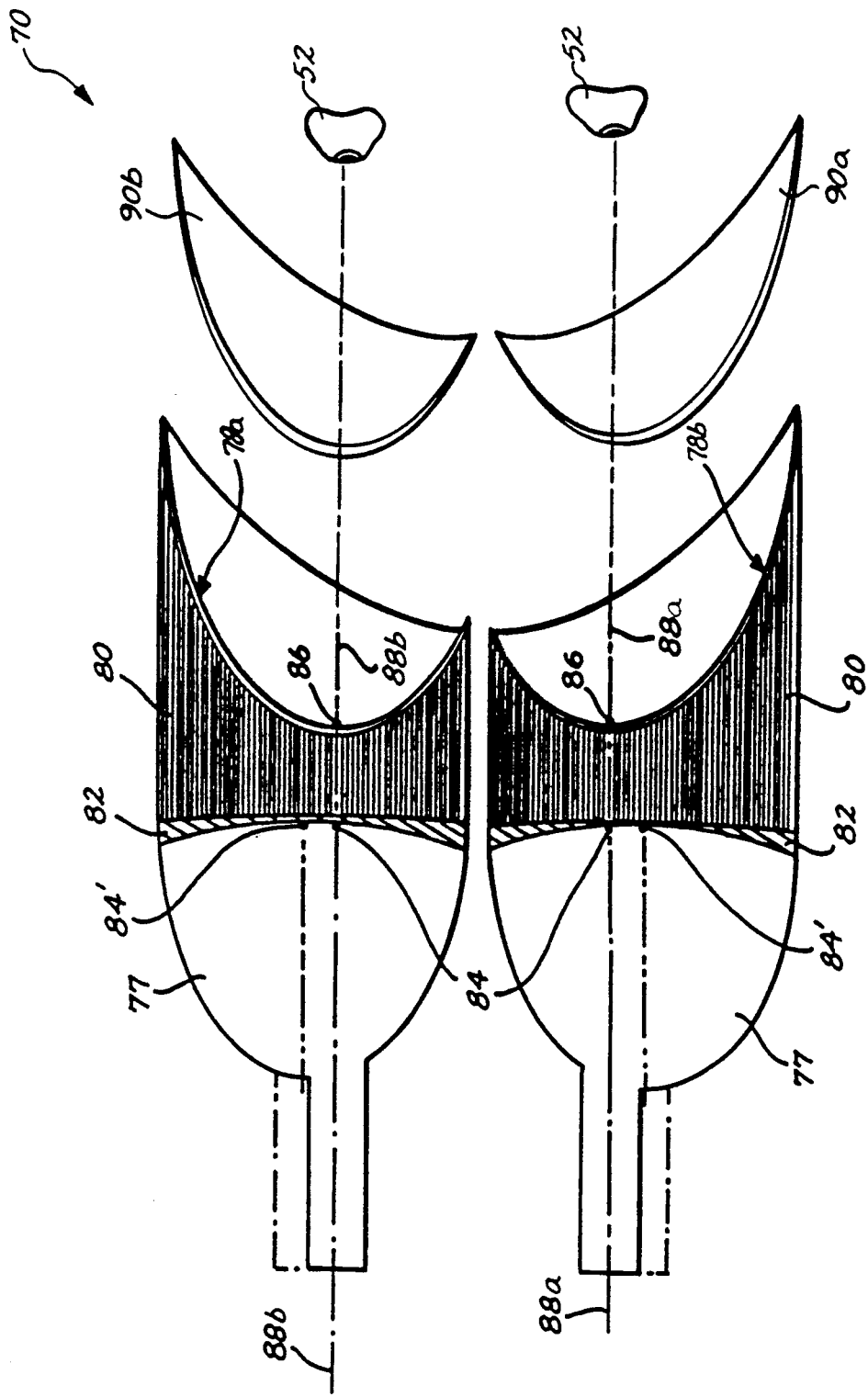
FIG. 8 is an exploded pictorial view of a third preferred embodiment of a stereoscopic viewing system in accordance with the invention.

With reference to FIG. 8, a stereoscopic viewing system 70 in accordance with the invention includes a pair of cathode ray tubes (CRTs) 77 that display images to a pair of screens 78a and 78b via fiber optic bundles 80 and interfaces 82. The fiber optic cables and interfaces allow images displayed on a flat surface (CRTs 77) to be displayed on a curved surface (screens 78). The interfaces 82 carry images from the CRTs 77 to the fiber optic bundles 80. The optical fibers in each fiber optic bundle 80 terminate opposite interfaces 82 to form the screens 78. The images displayed on the screens 78a and 78b are focused by optical components 90a and 90b, respectively.

The CRTs 77 and the screens 78 have centerlines 84 and 86, respectively, that are aligned with the centerlines of vision 88a and 88b of the eyes 52 of a viewer. The centerlines 84 are preferably aligned with the centerlines of vision 88 of the eyes by mechanically offsetting the video display CRT inputs as indicated in FIG. 8. An alternative embodiment utilizes symmetrical CRT inputs shown in reference with centerlines 84'. In the alternative embodiment, the images are electronically adjusted at the interfaces 82 to align the image centers with the screens' centerlines 86.

Figure 9:
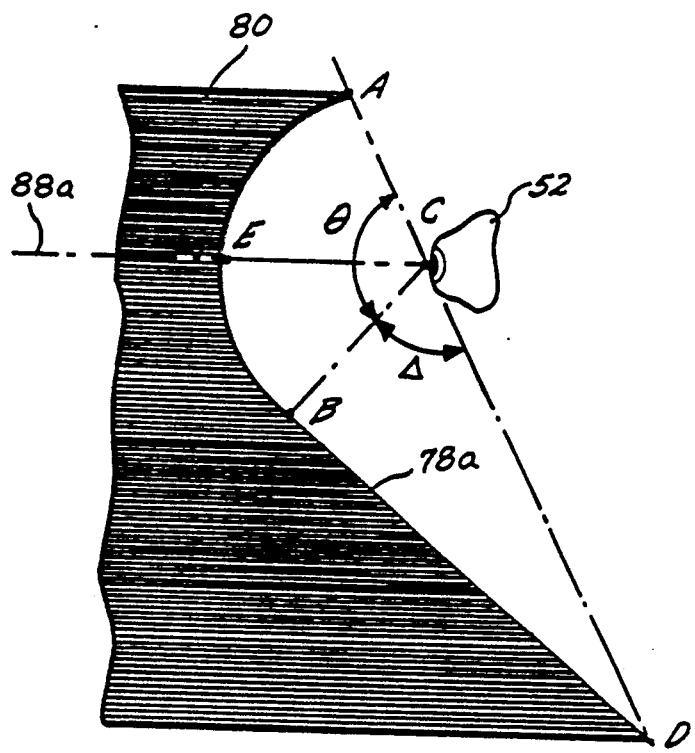
FIG. 9 is a cross-sectional view along a horizontal plane of the display component of FIG. 8, with the cross-sectional plane cutting through the centerline of vision of the viewer's eye.
Figure 10:
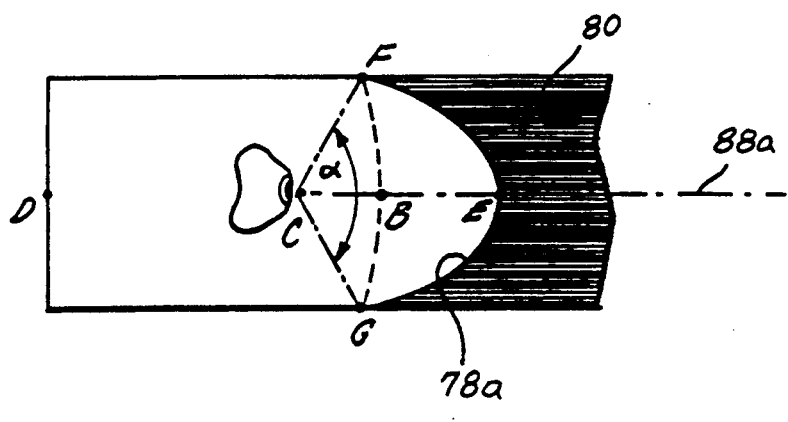
FIG. 10 is a side elevational view of a vertical cross section of the display component of FIG. 8.

The geometry of the screens 78 is illustrated in FIGS. 9 and 10. The below-described dimensions of the lenses provide the average viewer having an interpupillary distance of about 2.37 inches with the full field of view, as gathered by the image-gathering component. The dimensions of one preferred embodiment of the screens will be described in terms of left screen 78a. It is to be understood that right screen 78b is similarly dimensioned.

FIG. 9 is a cross-sectional top view of the left screen 78a, cut along a horizontal plane including the centerline of vision 88a. Screen 78a is defined as having a central surface and a cylindrical temporal surface. The central surface of the screen, i.e., between points A and B, is spherical with a radius on the order of 1.31 inches. The angle $\theta$ formed between lines AC and CB subtends 120°. The angle $\Delta$ formed between lines CB and CD subtends approximately 60°. In the preferred embodiment, line EC bisects angle ACB. Line BD is a relatively straight line and represents a line bisecting the length of the cylindrical temporal surface, with the radius of the cylinder defining the temporal surface being on the order of 1.31 inches. The temporal surface of the screen terminates at D. The angle formed by lines AC and CD subtends approximately 180°. Thus, the full horizontal field of vision is provided to the viewer.

FIG. 10 illustrates a cross-sectional side view of the left screen 78a, cut along a vertical plane including centerline of vision 88a. The cross section of the screen between F and G is spherical with a radius of 1.31 inches. FG is the line of intersection of the central surface and the temporal surface of screen 78a. The angle $\alpha$ formed by lines FC and CG is 120°, 60° above and below the centerline of vision 88a. Thus, screen 78a provides the full 120° vertical field of vision to the viewer. The side surface extends temporally with a constant radius of 1.31 inches from FG, to terminate at D of FIG. 9.

For the viewer with an interpupillary distance of about 2.37 inches, screens 78 with radii of 1.31 inches can be mounted side by side and in front of the viewer's eyes without interfering with one another or with the viewer's nose. The interpupillary distance for the average American adult is 2.36 to 2.71 inches. Screens for the average person would have radii between 1.1 and 1.36 inches. It is to be understood that the radii of the screens can vary beyond this average range, depending on facial characteristics such as nose size and interpupillary distance.

With reference again to FIG. 8, while the close proximity of the screens 78 allows the viewing of stereoscopic images, a form of optical correction is required to properly focus the displayed images to the viewer's eyes. To this end, the stereoscopic viewing system 70 includes an optical component 90 that provides the required correction without obstructing the images being viewed. Given a 1.31 inch radius for the screens 78, a 30 diopter correction will provide clear viewing for a person of normal eyesight, i.e., a person having 20/20 vision. This correction will bring the displayed images into focus, while the viewer's eyes remain relaxed and focused at infinity.

The optical component 90 for each screen 78 is of a similar, but slightly smaller geometry than that of the screens 78 so as to fit against the surface of each screen. The optical correction through the optical components 90 must be of adequate strength to adjust the perception of the curved screen surfaces to equal the viewer's natural focal length. Each optical component 90 comprises a plurality of converging lenses or elements, each having an exit pupil that is positioned in close proximity to the pupil of the eye. Individual lenses are not illustrated in FIG. 8. The lenses are preferably formed using holographic or microlithographic techniques that are known in the art.

In one embodiment, each optical component 90a and 90b is a substrate that includes a plurality of transmissive holographic optical elements. The holographic optical elements provide the desired optical correction, e.g., 30 diopters, to allow the eyes to properly focus on the screens 78. The substrates comprising the optical components 90a and 90b are approximately the shape of the surfaces of screens 78a and 78b, but have a slightly smaller geometry so as to fit flush against the surface of each screen. The characteristics of the 30 diopter lens correction are induced onto the substrate through methods known in the art and described below.

Current manufacturing techniques for making the optical components 90 using holographic techniques include, for example, forming an interference pattern from the intersection of a signal laser beam and a laser reference beam. This is accomplished by (1) sending the signal beam through a beam expander and subsequently through a lens system having the appropriate optical correction, e.g., 30 diopters, (2) sending the reference beam through a beam expander, (3) combining the expanded reference and signal beams, and (4) projecting the combined beams onto a surface of the substrate. The resultant optical component 90 thus acquires the characteristics of the (30 diopter) lens system. Thereafter, the optical component 90 is pressed or snapped against the surfaces of the screens 78.

A second method of holographically forming the optical component 90 is to use a small, e.g., 6 micron diameter laser beam. The signal laser beam is sent through a lens system of the appropriate optical correction and then combined with the reference beam. The resultant interference beam is then reflected from a mirror placed at the center radius of the optical component (corresponding to the center radius of the surfaces of the screens). The interference beam is pulsed to strike the mirror as the mirror is incrementally shifted to write individual holographic elements. The beam is simultaneously angled to intersect the optical component at the viewing angle appropriate for each element written. Each element has its own exit pupil positioned near the viewer's eye.

Figure 11:
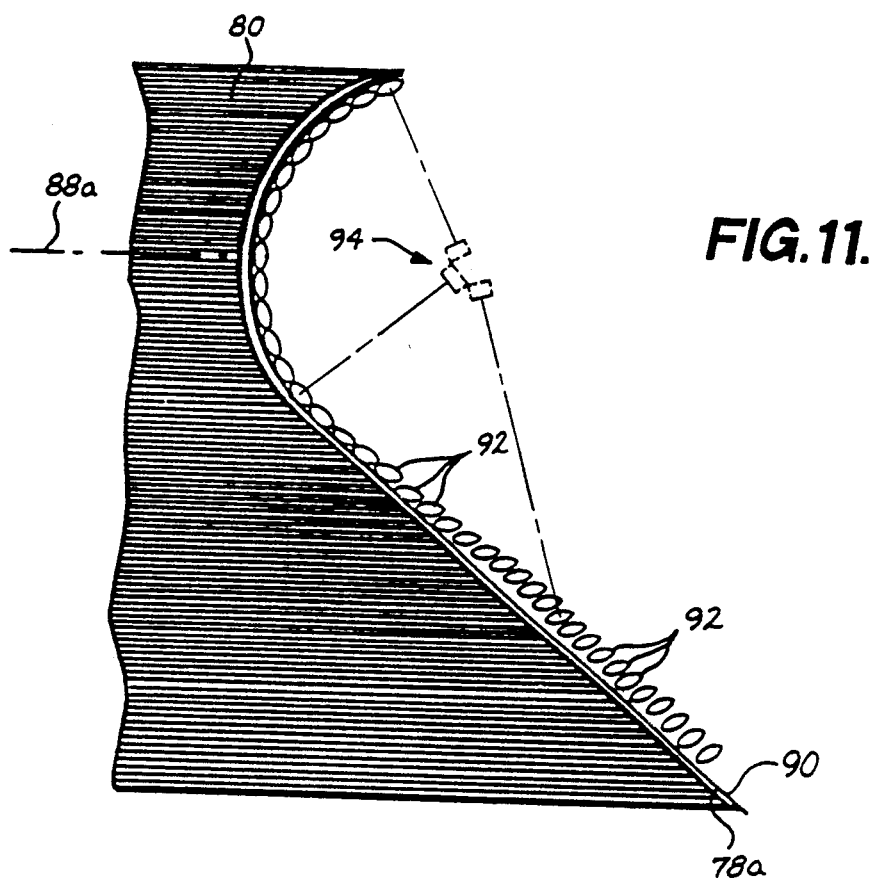
FIG. 11 illustrates an alternate optical component for use in the stereoscopic viewing system of FIG. 8.

With reference to FIG. 11, the optical component 90 may also be formed using microlithographic techniques. In this method, 30 diopter (or other appropriate diopter) lenslets 92 are etched into a polycarbonate substrate through techniques known in the art of microlithography. Thereafter, the substrate is attached to the screen and held against the screen's surface through clips or other appropriate holding devices. A suitable process for fabricating the optical component 90 using microlithographic techniques comprises (1) constructing a beryllium alloy master that includes the lenslets 92 and that has a similar geometry to that of the screens 78, and (2) vacuum or pressure molding a polycarbonate substrate of adequate refractive index onto the master, thereby inducing the lenslet configurations into the polycarbonate substrate.

Irrespective of the method used to form the optical component 90, the optical component will provide a plurality of exit pupils located near the pupil of the viewer's eye. In the first described holographically formed component, there will be as many exit pupils as there are optical fibers ending to form the screens. In the second described holographically formed component, each optical element has an exit pupil. In the microlithographically formed component, each lenslet includes an exit pupil. With reference to FIG. 11, the exit pupils 94 of three representative lenslets 92 are illustrated. As the eye 52 scans to see different portions of the displayed image, it will perceive the image through the exit pupils of the lenslets in the scanned area. Thus, the displayed image will be clearly focused by the display component 90. The exit pupils for the holographically formed optical components would have similar, although slightly smaller, dimensions than those illustrated in FIG. 11.

It is noted that the optical correction of the optical component 90 may be altered to accommodate viewers with myopia (nearsightedness) and hyperopia (farsightedness), as well as to accommodate different screen sizes.

With reference again to FIG. 8, the surfaces of screens 78 are preferably formed by smooth grinding the ends of the optical fibers in the fiber optic bundles 80. The ends of the optical fibers are then coated with a single layer of glass microbeads (not shown). The coating process comprises application of a viscous coating to the microbead layer, spraying the glass microbeads onto the coating, and subsequently removing the excess beads through air pressure or other suitable means. Thus, a single layer of beads are left clinging to the optical fiber ends. The microbeads diffuse the light emitting from the fiber optic cables, thereby allowing the images to be readily viewed by the eyes of a viewer.

A suitable viscous coating for attaching the microbeads is an ultraviolet setting optical epoxy. The epoxy is thinned to a consistency such that the epoxy is sprayable and will create a self-leveling glue layer across the fiber ends. Once the epoxy is applied, the thinner is allowed to evaporate from the glue layer. After the thinner has evaporated, the microbeads are sprayed onto the epoxy in a thickness adequate to ensure that the epoxy is completely covered. The epoxy is then hardened by subjecting the epoxy to ultraviolet light. After the epoxy is completely hardened, the excess microbeads are shaken loose and otherwise removed from the surface through air pressure. The single layer of microbeads remaining forms the screen surface.

The viscous coating preferably has no capillary attraction with the microbeads in order to prevent more than a single layer of the glass microbeads from adhering to the fiber ends. Capillary attraction of the microbeads during the screen manufacturing process is avoided by controlling the viscosity of the epoxy in relation to the diameter of the microbeads. The viscosity is preferably inversely proportional to the diameter of the microbeads. For example, in one actual embodiment, the microbead diameter is less than or equal to 7 microns. A suitable epoxy for use with these microbeads is Norland Optical Adhesive No. 68, available from Norland Products, Inc., of New Brunswick, N.J.

Figure 12:
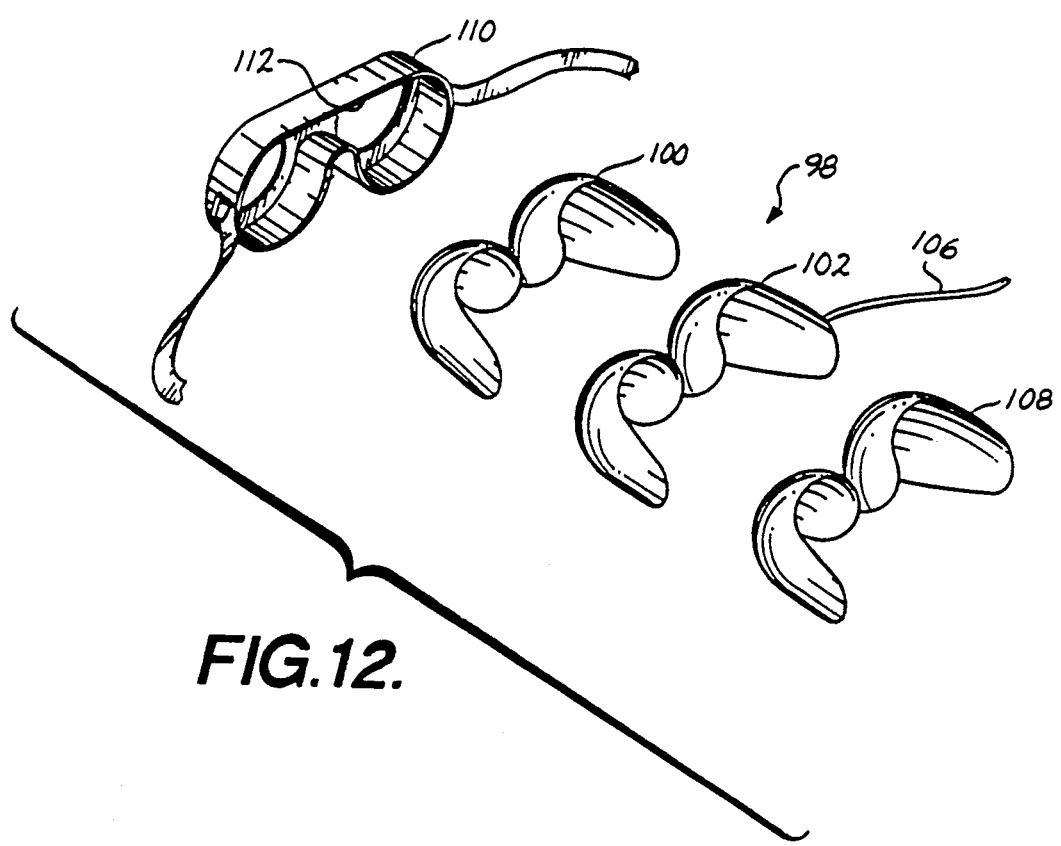
FIG. 12 is an exploded view of a fourth preferred embodiment of a stereoscopic viewing system in accordance with the invention.

With reference to FIG. 12, in a fourth preferred embodiment of the invention, a stereoscopic viewing system 98 includes a backing layer 100, an imaging layer 102, an image receiving component or cable 106, and an optical component 108. Each layer includes a left and right side. The dimensions of the backing layer 100 and imaging layer 102 are similar to the dimensions of screens 78 described above. Each of the components is relatively thin. Thus, the viewing system as a whole is relatively light weight.

The backing layer 100 is made of a rigid material such as glass and is used to support the imaging layer. The imaging layer 102 is preferably a light emitting diode (LED) display, liquid crystal display (LCD), or thin film image display layer. The imaging layer receives left and right image signals from the image processor (not shown) through the cable 106, which is a signal-carrying device. The optical component 108 is made using holographic, microlithographic or other available techniques, as described above, to focus the images displayed on imaging layer 102 to the eyes of a viewer.

In one preferred embodiment, the layers are secured within goggles 110. The edge 112 of the goggles is shaped so as to conform to an average viewer's face near the eyes, and acts to properly align the screen centers with the viewer's centerline of vision. Additionally, the goggles act to block out all aspects of actual reality so that the viewer's total visual reality is formed by the displayed images. As an alternative to the goggles 110, the layers are supported by a look-into device similar to that of FIG. 4 or in a helmet-mounted system.

Figure 13:
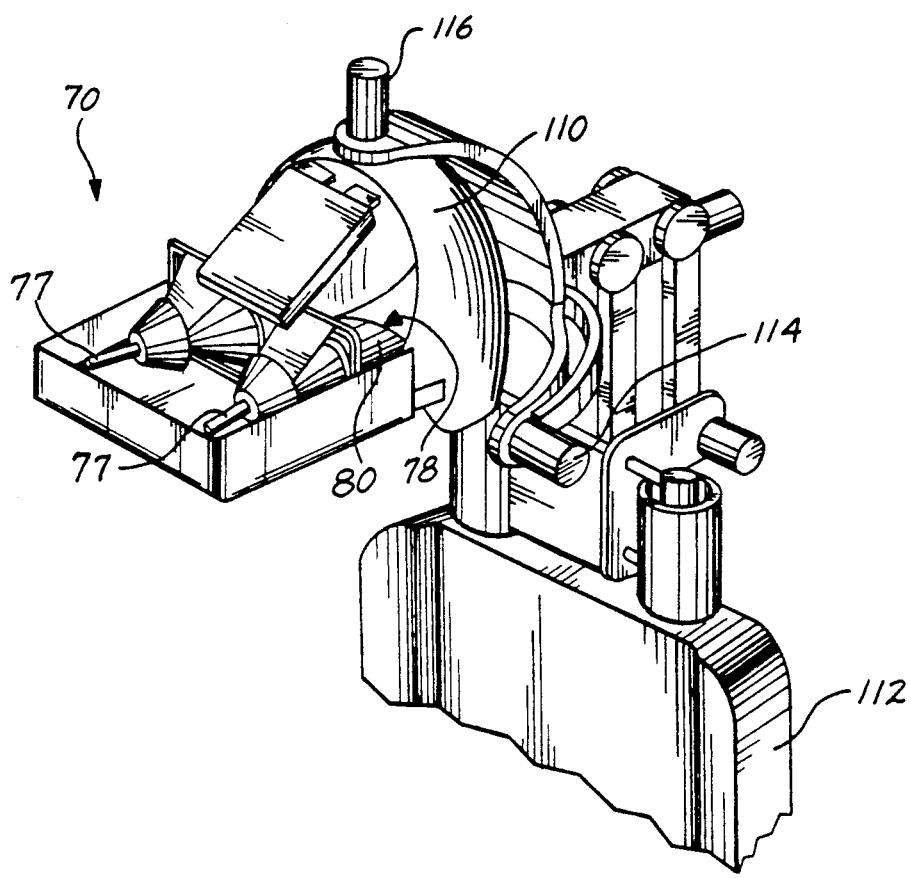
FIG. 13 is a pictorial view incorporating the stereoscopic viewing system of FIG. 8.

FIG. 13 illustrates an environmental embodiment of the stereoscopic viewing system 70 of FIG. 8. It is to be understood that a similar arrangement may be used for the stereoscopic viewing systems 30 and 98 of FIGS. 4 and 12, respectively. The stereoscopic viewing system 70 is mounted in a helmet 110 attached to a chair 112 by a frame that allows the helmet to pivot along a horizontal axis 114 and a vertical axis 116. The helmet 110 aids in blocking external indications of actual reality from viewer perception and in maintaining the relative orientation of the stereoscopic viewing system with respect to the viewer's head. Other devices that provide these functions can also be used. Motion detectors coupled to the horizontal and vertical axes 114 and 116 send signals to an image gatherer (not shown) that tracks the movement of the helmet. Thus, a user sitting in the chair 112 and having his or her head positioned in the helmet 110 can view objects dispersed about an area in which the image gatherer is located using normal head movement. In one embodiment, the image gatherer is mounted on a remote unit controlled by a joystick on the arm of the chair to provide remote exploring capability.

It is noted that in FIG. 13 the viewer's head is stationary relative to the stereoscopic viewing system 70. As the head, helmet and viewing system are rotated along the horizontal and vertical axis, the field of view is being changed in corresponding increments with the head (through the tracking of the image gatherer). Thus, while the field of view is defined above with respect to a stationary head, providing for head movement is consistent with this definition because there is a one-to-one correspondence between the head movement and field of view perceived by the eyes.

Although the present invention has been described with respect to its preferred embodiments, those skilled in the art will realize that changes may be made in form and scope without departing from the spirit of the invention. Therefore, the scope of the invention should be determined solely by reference to the following claims.

The embodiments of the invention in which an exclusive property or privilege is claimed are defined as follows:

1. Apparatus for the viewing of images by an eye of a viewer, the eye having a field of view defined with respect to the viewer's head being stationary and the eye free to rotate in its socket, the field of view including an area of visual attention where objects may be perceived with detail and sharpness and an area of peripheral vision falling outside the area of visual attention but still perceptible by the eye as it scans the area of visual attention, the apparatus comprising:
   an image display component including (a) means for receiving signals representative of first and second images to be viewed, (b) first and second display surfaces, and (c) means for displaying the first and second images on the first and second display surfaces, respectively; and
   means for focusing the images displayed on the first and second display surfaces to a single eye of a viewer, said means for focusing including first and second optical systems, each optical system including an exit pupil, the first optical system conveying light from the first display surface to the exit pupil of the first optical system, and the second optical system conveying light from the second display surface to the exit pupil of the second optical system, such that when the viewer's eye is positioned within the exit pupils, the field of view includes an image comprised of the first and second images.

2. The apparatus of claim 1, wherein the first optical system focuses images from the first display surface primarily to the area of visual attention of the eye and the second optical system focuses images from the second display surface primarily to the area of peripheral vision of the eye.

3. The apparatus of claim 2, further including means for gathering the signals representative of the first and second images to be viewed, said means for gathering comprising first and second cameras, the first camera gathering images to be displayed primarily at the first display surface and the second camera gathering images to be displayed primarily at the second display surface.

4. The apparatus of claim 1, including mounting means for aligning the display surfaces relative to the viewer's eye such that the viewer's eye is within the exit pupils of the first and second optical systems.

5. Apparatus for the viewing of images by a viewer, the viewer's eye having a field of view defined with respect to the viewer's head being stationary and the eye free to rotate in its socket, the field of view including an area of visual attention where objects may be perceived with detail and sharpness and an area of peripheral vision falling outside the area of visual attention but still perceptible by the eye as it scans the area of visual attention, the apparatus comprising:

an image display component including (a) means for receiving signals representative of images to be viewed, (b) a concave display surface, the display surface having a first surface area for displaying images within the area of visual attention and a second surface area for displaying images within the area of peripheral vision, (c) means for displaying images on the first and second surface areas of the display surface; and optical means for focusing the images displayed on the display surface surface to the eye.

6. The apparatus of claim 5, wherein the optical means includes a plurality of exit pupils such that the viewer's eye, when positioned within the exit pupils, can perceive images displayed on the display surface.

7. The apparatus of claim 6, wherein the optical means is a substrate comprising a plurality of holographically formed optical elements.

8. The apparatus of claim 6, wherein the optical means is a substrate comprising a plurality of microlithographically formed optical elements.

9. The apparatus of claim 6, wherein the apparatus further includes mounting means for aligning the display surfaces relative to the viewer's head such that the viewer's eye is positioned within the exit pupils of the optical means.

10. The apparatus of claim 5, further including means for gathering the signals representative of the images to be viewed, said means for gathering comprising first and second cameras, the first camera gathering images to be displayed to the first surface area of the display surface and the second camera gathering images to be displayed to the second surface area of the display surface.

11. The apparatus of claim 5, wherein the display surface includes a temporal edge and the first surface area of the display surface is spherical with radius R and the second surface area is a continuous cylindrical extension of the first surface area toward the temporal edge of the display surface, with the radius of the cylindrical extension being radius R.

12. The apparatus of claim 11, wherein the radius R is less than or equal to one-half the interpupillary distance of the viewer.

13. The apparatus of claim 11, wherein the display surface is comprised of optical fibers.

14. The apparatus of claim 13, wherein the display surface comprises optical fiber ends coated with a single layer of glass microbeads.

15. Apparatus for the viewing of stereoscopic images by a viewer, each of the viewer's eyes having a field of view defined respect to the viewer's head being stationary and the eye free to rotate in its socket, the field of view for each eye including an area of visual attention where objects may be perceived with detail and sharpness and an area of peripheral vision falling outside the area of visual attention but still perceptible by the eye as it scans the area of visual attention, the apparatus comprising:

an image display component including (a) means for receiving signals representative of separate left and right images, (b) left and right concave display surfaces, each display surface having a first surface area for displaying images within the area of visual attention and a second surface area for displaying images within the area of peripheral vision, and (c) means for displaying the left and right images on the display surfaces; and left and right means for focusing the images displayed on the display surfaces to the eyes of the viewer, the left and right focusing means each including a plurality of exit pupils located near the viewer's eye such that the eye, when positioned in the exit pupils, perceives the image displayed on the corresponding display surfaces.

16. The apparatus of claim 15, wherein the left and right focusing means include left and right substrates, respectively, each substrate comprising a plurality of holographically formed optical elements.

17. The apparatus of claim 15, wherein the left and right focusing means include left and right substrates, respectively, each substrate comprising a plurality of microlithographically formed optical elements.

18. The apparatus of claim 15, wherein the apparatus further includes mounting means for aligning the display surfaces relative to the viewer's head such that the eyes are positioned within the exit pupils of the left and right focusing means.

19. Apparatus for the viewing of stereoscopic images by a viewer, each of the viewer's eyes having a field of view defined with respect to the viewer's head being stationary and the eye free to rotate in its socket, the field of view for each eye including an area of visual attention where objects may be perceived with detail and sharpness and an area of peripheral vision falling outside the area of visual attention but still perceptible by the eye as it scans the area of visual attention, the apparatus comprising:

left and right image display components, each image display component including (a) means for receiving signals representative of first and second images to be viewed, (b) first and second display surfaces, and (c) means for displaying the first and second images on the first and second display surfaces, respectively; and left and right optical components for focusing the images displayed on the first and second display surfaces of the left and right image display components to the left and right eyes, respectively, each of the optical components including first and second optical systems, each optical system including an exit pupil, the first optical system conveying light from the first display surface to the exit pupil of the first optical system, and the second optical system conveying light from the second display surface to the exit pupil of the second optical system, such that when the viewer's eyes are positioned within the exit pupils, the left and right fields of view include images comprised of the first and second left and right images, respectively.

20. The apparatus of claim 19, including mounting means for aligning the display surfaces relative to the viewer's eyes such that the left eye perceives the first and second images displayed on the display surfaces of the left image display component through the exit pupils of the first and second optical systems of the left optical component, respectively, and the right eye perceives the first and second images displayed on the display surfaces of the right image display component through the exit pupils of the first and second optical systems of the right optical component, respectively.

21. The apparatus of claim 19, further including means for gathering the signals representative of the first and second images to be viewed by each eye, said means for gathering comprising first and second cameras for each eye, the first camera gathering images to be displayed primarily to the area of visual attention and the second camera gathering images to be displayed primarily to the area of peripheral vision.

* * * * *

UNITED STATES PATENT AND TRADEMARK OFFICE
CERTIFICATE OF CORRECTION

PATENT NO. : 5,274,405
DATED : December 28, 1993
INVENTOR(S) : J.A. Webster It is certified that error appears in the above-identified patent and that said Letters Patent is hereby corrected as shown below:

| COLUMN | LINE | |
|---|---|---|
| 1 | 6 | "DAAHO1-89-C0242" should read --DAAH01-89-C0242-- |
| 2 | 60 | "by" should read --may be-- |
| 15 (Claim 5 | 16 Line 20) | delete "surface" (second occurrence) |

Signed and Sealed this

Twenty-eighth Day of June, 1994

Attest:

BRUCE LEHMAN

*Attesting Officer*    *Commissioner of Patents and Trademarks*